US006348349B1

(12) United States Patent
Bruggemann

(10) Patent No.: US 6,348,349 B1
(45) Date of Patent: *Feb. 19, 2002

(54) YEAST ARTIFICIAL CHROMOSOMES AND THEIR USE IN THE CONTROL OF GENE EXPRESSION

(75) Inventor: Marianne Bruggemann, Foxton (GB)

(73) Assignee: The Babraham Institute (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/110,811

(22) Filed: Jul. 6, 1998

Related U.S. Application Data

(63) Continuation of application No. 08/204,294, filed as application No. PCT/GB92/01651 on Sep. 10, 1992.

(30) Foreign Application Priority Data

Sep. 10, 1991 (GB) ............................................. 9119338

(51) Int. Cl.⁷ ................................................ C12N 5/10
(52) U.S. Cl. ...................................................... 435/325
(58) Field of Search ............................. 435/320.1, 325; 530/23.1, 23.2, 23.7

(56) References Cited

FOREIGN PATENT DOCUMENTS

| EP | 0264166 | of 0000 |
|---|---|---|
| EP | 0375406 | of 0000 |
| WO | 8801648 | of 0000 |
| WO | 8810118 | of 0000 |
| WO | 8912823 | of 0000 |
| WO | 9004036 | of 0000 |
| WO | 9203918 | of 0000 |
| WO | WO 94/23049 | * 10/1994 |

OTHER PUBLICATIONS

Huxley et al. The human HPRT gene on a yeast artificial chromosome is functional when transferred to mouse cells by cell fusion. Genomics vol. 9, pp. 742–750, 1991.*
Capecchi the new mouse genetics: Altering the genome by gene targeting. Trends in Genetics vol. 5 pp. 70–76, 1989.*
Burke et al. Cloning of large segments of exogenous DNA into yeast by means of artificial chromosome vectors. Science vol. 236 pp. 806–812, 1987.*
Bradley Modifying the mammalian genome by gene targeting. Current Opinion in Biotechnology vol. 2 pp. 823–829, 1991.*
Davies et al. Nucleic Acids Research, vol. 20(10):2693–2698, Jun. 11, 1992.
Schedl et al. Nucleic Acids Research, vol. 20(12):3073–3077, Jul. 13, 1992.
Roth Naturwissenschaften, vol. 74(2):78–85, Feb. 1987.
Strauss et al. EMBO Journal, vol. 11(2):417–422, Feb. 1992.
Gnirke et al. EMBO Journal, vol. 10(7):1629–1634, Jul. 1991.
Elicieri et al. Proceedings of the National Academy of Science, vol. 88:2179–2183, Mar. 1991.
Pachnis et al. Proceedings of the National Academy of Science, vol. 87:5109–5113, Jul. 1990.
Nelson et al. Proceedings of the National Academy of Sciences, vol. 86:6686–6690, Sep. 1989.
Srivastava et al. Gene vol. 103:53–59, 1991.
Brinster et al. Nature, vol. 306:332–336, Nov. 24, 1983.
Kenichi et al. Biochem.Genetics, vol. 101:149, 1984, item No. 205251h.
Pavan et al. Molecular Cell Biology, vol. 10(8):4163–4169, Aug. 1990.
Davies et al. (1993) "Creation of Mice Expressing Human Antibody Light Chains by Introducion of a yeast Artificial Chromosome Containing the Core Region of the Human Immunoglobulin k Losus" Bio/Technology 11:911–914.
Davies, Nicholas Paul (1993) "Modification, transfer and expression of yeast artificial chromosomes carrying human immunoglobulin genes" Doctor of Philosophy Dissertation submitted to the University of Cambridge, Oct. 1993.
Macina, Roberto A., Harold C. Riethman (1992) "Direct DNA Hybridization Screening of Primary Yeast Transformants in the Construction of Targeted Yeast Artificial Chromosomes (YAC) Libraries" GATA 9(2):58–63.

* cited by examiner

Primary Examiner—John S. Brusca
(74) Attorney, Agent, or Firm—Saliwanchik, Lloyd & Saliwanchik

(57) ABSTRACT

Embryonic stem cells or other cells (not prokaryotic or yeast) that are essentially free of yeast DNA are prepared from suitably marked yeast artificial chromosomes and used to transfer DNA segments of considerable size into organisms.

8 Claims, No Drawings

YEAST ARTIFICIAL CHROMOSOMES AND THEIR USE IN THE CONTROL OF GENE EXPRESSION

This application is a continuation of application Ser. No. 08/204,294, filed Mar. 7, 1994, now U.S. Pat. NO. 5,776,773, which was the national stage of International Application No. PCT/GB92/01651, filed Sep. 10, 1992.

FIELD OF THE INVENTION

This invention relates to yeast artificial chromosomes and their manipulation and transfer into cells and animals, to exploit the control of gene expression, and also to the resulting cells and animals.

BACKGROUND OF THE INVENTION

The ability to transform suitable hosts with foreign DNA, and thus to express gene products not normally produced by the host, is an important goal of biotechnological research. Microorganisms can be used to produce desired proteins, while higher animals having desirable characteristics have also been produced. For example, EP-A-0264166, WO-A-8800239, WO-A-8801648, WO-A-9005188 and WO-A-9211358 describe the use of lactating animals to express foreign proteins which are produced in the milk and can be isolated therefrom; this provides a very satisfactory, controlled source of pure protein.

Techniques to transfer cloned DNA into mammalian cells and transgenic animals have greatly facilitated the study of gene regulation and expression. Gene transfection experiments have also highlighted the fact that the limited size of many cloned DNA molecules prevents the efficient use of the numerous distant regulatory sequences believed to control expression.

More particularly, in order to investigate regulation of complex loci and chromosomal domains harbouring clusters of genes, it is essential to introduce very large pieces of DNA into cells and animals. The conventional approaches used in transgenic animal technology have limitations, making it difficult to introduce DNA fragments which are greater than 100 kb; see Brüggemann et al, Eur. J. Immunol. 21:1323–1326 (1991). For example, while germ line-dependent genomic imprinting may affect large areas in which a number of genes may be similarly regulated, there is no efficient method to study such "imprinted" domains. A satisfactory technique for introducing large DNA fragments would allow progress, and also facilitate the analysis of other complex loci such as the T-complex (harbouring specific deletions) for which a number of genes have been mapped which are crucial for mammalian development. In order to obtain a better understanding of the regulation of eukaryotic genes, it would be desirable to express these genes in their authentic genomic context after cloning and re-introduction into cells.

The expression of mammalian genes is controlled at various levels: the genomic context (influence of neighbouring genes), regulatory elements proximal to the exons (e.g. promoters), regulatory sequences downstream of the termination codon (polyadenylation site) and regulatory motifs further away from coding sequences (e.g. enhancers). For immunoglobulin genes, it has been shown that expression of transgenes is poor when enhancer motifs are missing, and that these can be several thousand base-pairs away (25 kb for the heavy chain 3'-enhancer) from the nearest exon.

Mouse models have been established to address the question of the immunogenicity of chimaeric, foreign and authentic antibodies used for therapeutic purposes; see Brüggemann et al, J. Exp. Med. 170:2153 (1989). It became clear that only authentic proteins escape the surveillance of the immune system.

The techniques currently used for making human antibodies involve either in vitro immunisation and immortalisation of human lymphocytes or genetic engineering. The selection of rare specific antibody-producing human lymphocytes outside the body is difficult and, once the lines are obtained, their yield and stability are poor; see Borrebaeck, Immunol. Today 9:355 (1988). Genetic engineering (also termed "humanisation" of rodent antibodies) firstly has to be done for each individual mouse or rat antibody of therapeutic use and secondly does not yield completely human antibodies; see Riechmann et al, Nature 332:323 (1988). "Humanising" existing rodent antibodies already approved for therapy is currently the most successful way to obtain less immunogenic reagents. However, it would be a considerable improvement to have a mouse strain available which makes authentic human antibodies after immunisation with human materials.

A repertoire of immunoglobulins has been obtained from transgenic mice carrying inserted human antibody gene segments in germ line configuration; see WO-A-9004036 and Brüggemann et al, PNAS 86:6709 (1989). A human mini IgH locus has been constructed with variable region genes (Vs), diversity segments (Ds), joining segments (Js) and the $\mu$ constant region gene (C$\mu$). The human gene segments rearrange in the lymphoid tissue of these mice (VDJ-C$\mu$) and antibodies with human $\mu$ heavy chains can be obtained after immunisation. However, the level of human IgM as opposed to mouse IgM is low, and specific hybridomas with human $\mu$ chains are rare after immunisation. A further complication is that most of those cells that produce human heavy chain also secrete endogenous mouse Ig. This means that rearrangement of human $\mu$ does not stop endogenous rearrangement; in other words, allelic exclusion is not achieved. Furthermore, the actual repertoire size of the produced human antibodies is unknown but might be small as the IgH construct contains only a limited number of V an: D segments.

Srivastava et al, Gene 103:53–59 (1991), describe plasmids which permit the insertion of neomycin-resistance gene into the human DNA insert or the vector arm of a YAC. In the latter case, the plasmid also contains a LYS2 gene for selection in a yeast host. The URA3 gene is then replaced by a new insert, thus inactivating URA.

Bothstein et al, Science 240:1439–1443 (1988), describe the practical advantages of the yeast organism for cloning and manipulating large DNA molecules. Green et al, Science 250:94–98 (1990), report the cloning of segments c. us to one million base-pairs in yeast cells in artificial chromosomes (YACs), allowing the long-range mapping and analysis of complex genomes. Yeast vectors for cloning of large DNA molecules combine two features; plasmid sequences for their propagation in *E. coli* and yeast specific sequences to ensure the replication and maintenance of a linear molecule when grown in yeast.

Nevertheless, the problem of producing large molecules (of which specific examples are immunoglobulins, Factor VIII and Factor IX) on a commercial scale, remains. At the molecular level, it would be desirable to introduce large DNA molecules containing single genes of considerable size, in order to facilitate correct expression. For example, the human Ig heavy chain locus accommodating all Vs, Ds, Js and C regions is estimated to spread over 3000 kb of DNA; the Factor VIII gene is almost 200 kb in size with 23 exons. At present, high level of expression is rarely achieved by the introduction of cDNAs and engineers genomic "minigenes" into transgenic animals.

SUMMARY OF THE INVENTION

Surprisingly, it has now been found that specific DNA of considerable length can be introduced into ES cells via a YAC, without introducing DNA from the yeast. The need to purify the YAC out of yeast is thus avoided, and transformation is essentially foolproof. This discovery is applicable to the introduction of such DNA into other cells also.

The appropriate YAC, for use in the present invention, includes a foreign gene or gene locus (i.e. including one or more genes or gene segments) of at least 100 kb and also a marker gene which allows selection in cells that are not prokaryotic or yeast cells. This construct can be obtained by integration of the marker gene, e.g. Neo, into a YAC including the foreign gene.

In a further aspect of the invention, ES cells or other cells are transformed by the marked YAC, and thus can be selected and inserted into, say, animals which consequently express human immunoglobulin or other genes. In particular, a transgenic lactating, ovine cr bovine animal, mouse or other rodent, or any non-human animal, may contain a foreign gene or gene locus of considerable length, e.g. at least 100 kb, often at least 300 kb, but also 1 Mb or more, if required. The animal may express the product of another animal, e.g. a human product, but not its own corresponding product.

DESCRIPTION OF THE INVENTION

The available YACs contain a marker gene that allows for selection in prokaryotic cells, e.g. for ampicillin-resistance, but do not contain a marker gene that would allow for selection for integration in eukaryotic, ES, somatic or mammalian cells. This invention utilises the recombination proficiency of yeast to introduce an antibiotic resistance into the YAC by recombination. For example, neomycin-resistance gene controlled by the thymidine kinase promoter (neo) will allow selection in mammalian cells. Other suitable markers are hygromycin and HPRT-resistance. Depending on the circumstances, it may be desirable to prepare YACs with different markers, for integration.

The present invention is based in part on the realisation that yeast vectors with dominant selectable marker genes allow targeted integration into left (centromeric) and right (non-centromeric) YAC arms as well as alterations to human-derived insert DNA. In transformation experiments, integration proceeds exclusively by homologous recombination, although yeast prefers linear ends of homology for predefined insertions. Targeted regions can be rescued which expedite the cloning of internal human sequences and the identification of 5' and 3' YAC/insert borders. Integration of, say, the neomycin-resistance gene into various parts of the YAC allows the transfer and stable integration, and also rescue, of large DNA molecules into a variety of mammalian cells including embryonic stem cells.

The present invention utilises YACs as cloning vehicles for the complete integration of DNA of a length that has previously been difficult to transfer. The invention also allows specific modification of the DNA.

It may be necessary to enlarge an existing YAC containing heavy and light chain genes. A variety of human heavy and light chain-containing cosmids is available; they may be added on to the YAC by homologous, site-specific or other integration. Further, YACs containing different or overlapping parts of defined loci may be crossed, in order to obtain a contiguous DNA molecule in one YAC. This allows a large part of the human heavy and light-chain gene clusters to be reconstituted, and to obtain transgenic animals which make authentic human antibodies.

Similarly, a Factor IX-containing YAC may be modified in order to direct expression, for example, in milk. This may involve exchanging the Factor IX promoter for a mile: gene promoter, e.g. the murine whey acidic protein gene promoter, by homologous recombination in yeast. Factor VIII is another product that can be produced in the same way.

It is an important feature of the invention that the marker gene is incorporated into YAC in an active form, in order to allot selection. For this purpose, the YAC without that marker is subjected to integration with a plasmid containing the marker gene and a sequence outside the foreign gene, e.g. the ampicillin-resistance gene. This may lead to a YAC containing multiple copies of both markers, and duplication at least is preference, but the important point is that, say, neomycin-resistance can be observed.

The starting materials and techniques for use in the invention are generally known, or the materials can be prepared by known techniques. For example, several separately-derived embryonic stem (ES) cell lines are available: see Mansour et al, Nature 336:34E (1988); Schwartzberg et al, Science 246:799 (1989); Johnson et al, Science 245:1234 (1989); and Zijlstra et al, Nature 342:435 (1989). Transformation and selection procedures have already been established. Immunoglobulin genes on YACs are available, as is a YAC containing the Factor IX gene; these clones have been obtained independently by screening various YAC libraries; see Little et al, PNAS USA 86:1598 (1989). The sizes for the YACs vary and are between 200 and 600 kb. Cosmids may increase size to, say, 1.8 Mb.

The methods concerned with the introduction of large DNA molecules into cells are microinjection and coprecipitation with calcium phosphate (using any naked DNA such as YACs, genomic DNA or dissected chromosomes) or protoplast fusion, using yeast protoplasts: see Oi et al, PNAS USA 80:825–829 (1983); Graham and van der Eb, Virol. 52:456–658 (1973); and Richa and Lo, Science 245:175–177 (1989). The approach of directly injecting large DNA. molecules into fertilised eggs or ES cells was difficult because of the nature of DNA (large molecules are sticky). It is preferred to introduce the various YACs by protoplast fusion; this, however, needs the introduction of a selective marker gene into the YAC (see below). Another approach is the transfection of high molecular weight DNA or chromosomal DNA, mixed with selective marker DNA, into ES cells by calcium, phosphate co-precipitation. Identification of integrated genes of interest could then be done by probing with human Alu repeat sequences, confirming integration and size, as well as with specific probes. This random approach is similar to a library screening and depends on the transfection frequencies. Multiple copies of selective marker genes may thus be produced.

It is a primary object of the invention to introduce large DNA molecules into the germ line of mice or other non-human animals, e.g. via ES cells. For the purposes of this invention, such large molecules should be introduced in germ line configuration. By introducing thee into ES cells, the germ line locus, e.g. for antibodies or immunoglobulins, rearranges in the lymphoid tissue cf the animal, and thus antibody production takes place.

Techniques outlined above make use of YACs that contain, for example, well-characterised parts of the human immunoglobulin light and heavy chain loci or the Factor IX gene. In addition, high molecular weight DNA carrying any (large) genes of interest may be transferred into a variety of cells, including ES cells which can and have been used to obtain transgenic mice.

The purpose of introducing coding sequences and flanking regions on large DNA molecules is to preserve the original genomic context which facilitates the correct expression. These techniques also allow the introduction and study of large gene families. In combination with gene targeting, authentic foreign proteins can be obtained in large yield without interference of the homologous endogenbus gene products. In that way, an animal may be obtained with an immune system (in respect of antibody production) indistinguishable from that of man.

The endogenous mouse antibodies may interfere with the transgenic human immunoglobulins. It may therefore be necessary to silence the mouse immunoglobulin heavy and light chain loci by gene targeting in ES cells. A mouse strain can then be obtained with a transgenic human immunoglobulin heavy and light chain gene cluster, that makes no antibodies of its own.

In a particular example of the invention, a neomycin resistance cassette was integrated into a large (300 kb) YAC. The YAC contains a well-characterised region of the human immunoglobulin (Ig) kappa (κ) light chain locus. The modified IGκ YAC was transferred into embryonic stem (ES) cell lines by spheroplast fusion. The approach is useful for the transfer and expression of large genes and gene families in their original genomic context into the germline of other species via ES cells.

The κ locus in humans is estimated to spread over 2500 thousand base-pairs of DNA. The genes of the immunoglobulin κ light chain are assembled during B-cell differentiation by somatic recombination: one cf the many $V_\kappa$ (V=variable) gene segments rearranges with one of the five $J_\kappa$ (J=joining) segments, and a $C_\kappa$ (C=constant region) polypeptide is transcribed. In order to investigate the expression of such complex loci, it is essential to introduce very large fragments, containing many gene segments as well as necessary regulatory sequences, into cells and animals.

ES cells are suitable for gene manipulation experiments such as the introduction of large DNA molecules on YACs. Furthermore, ES cells can be reintroduced into blastocysts, and chimaeric and germline mice which carry the introduced loci can be derived from them.

The invention is further illustrated by the specific description that follows, and also by the Materials and Methods section of Davies et al, Nucleic Acids Research 20(11):2693–2698 (1992). The contents of that article are incorporated herein by reference.

The YAC containing the human K locus does not contain a marker gene which allows selection in ES cells. Therefore, in accordance with one embodiment of the invention, the neomycin resistance gene (neo) was integrated into the YAC. The neo gene permits selection of stable clones when transferred into mammalian cells. An example of the yeast-selectable marker gene that is also usually used is LYS2 which allows growth in lysine-deficient yeast media. Integration of exogenous DNA in yeast proceeds in an homologous fashion, and introducing new sequences into YACs, termed "retrofitting" by Eliceiri et al, PNAS USA 88:2179–2183 (1991) is facilitated because of the plasmid homology region of the YAC arms.

Targeted integration in yeast is either performed using replacement constructs or integration vectors; see Scherer et al, PNAS USA 76:4951–4955 (1979); Pavan et al, Mol. Cell. Biol. 10:4163–4169 (1990), and PNAS USA 88:7788–7791 (1991); and Srivastava et al, supra. Replacement vectors are designed to disrupt a region of homology by the insertion of exogenous DNA. In the particular example, homologous integration into YACs was studied using integration vectors which recombine as a whole and duplicate a given target sequence without impairing its function. Integration vectors can be rescued from YACs and also from transfected cells, as the bacterial sequences allow subcloning in bacteria, for example, and this permits the isolation of flanking insert DNA. The universal principle of integration using a set of vectors, several targeting sites and different YACs is shown. The modified YACs have been stably introduced into embryonic stem cells: thus, the experiments show the feasibility of transferring complex gene loci from one species to another.

An important aspect of the evidence is that YACs can be used to transfer such loci into other cells, without transferring potentially-undesirable yeast DNA, while retaining the locus in its essential configuration and size.

What is claimed is:

1. A murine embryonic stem cell, transformed with a foreign gene or gene locus of at least 100 kb wherein said cell is essentially free of yeast DNA.

2. The cell according to claim 1, wherein said cell further comprises a marker gene.

3. The cell according to claim 2, comprising at least two copies of said marker gene.

4. The cell according to claim 2, wherein said marker is for resistance to neomycin, hygromycin, or HPRT.

5. The cell according to claim 2, wherein the marker gene is in addition to an ampicillin-resistance or other prokaryotic selective marker gene and/or uracil-resistance or other yeast-selective marker gene.

6. The cell according to claim 1, wherein the foreign gene or gene locus is in germ line configuration.

7. The cell according to claim 1, wherein the foreign gene or gene locus is of al least 1 Mb.

8. A murine embryonic stem cell, comprising a foreign gene or gene locus of at least 100 kb and a marker gene, separate from the foreign gene or gene locus, which allows selection by one or more properties in the cell, wherein said cell is essentially free of yeast DNA.

* * * * *